United States Patent [19]

Hughes

[11] Patent Number: 5,679,805
[45] Date of Patent: Oct. 21, 1997

[54] PHOTOCHROMIC SPIRONAPHTHOPYRAN COMPOUNDS

[75] Inventor: Frank J. Hughes, Edina, Minn.

[73] Assignee: Vision-Ease Lens, Inc., Brooklyn Center, Minn.

[21] Appl. No.: 477,138

[22] Filed: Jun. 7, 1995

[51] Int. Cl.⁶ .................... C07D 309/32; C07D 335/14
[52] U.S. Cl. .................... 549/331; 549/26; 544/6
[58] Field of Search .................... 549/331, 26; 252/586; 544/6

[56] References Cited

U.S. PATENT DOCUMENTS

| | | |
|---|---|---|
| 3,567,607 | 3/1971 | Saunders et al. |
| 4,818,096 | 4/1989 | Heller et al. |
| 4,826,977 | 5/1989 | Heller et al. |
| 4,931,221 | 6/1990 | Heller |
| 4,980,089 | 12/1990 | Heller |
| 5,066,818 | 11/1991 | Gemert et al. |
| 5,106,998 | 4/1992 | Tanaka et al. |
| 5,238,981 | 8/1993 | Knowles |
| 5,244,602 | 9/1993 | Van Gemert |
| 5,274,132 | 12/1993 | VanGemert |
| 5,395,567 | 3/1995 | Van Gemert et al. |

FOREIGN PATENT DOCUMENTS 1451332   9/1966   France.

*Primary Examiner*—Nicky Chan
*Attorney, Agent, or Firm*—Kinney & Lange, P.A.

[57] ABSTRACT

A naphthopyran compound represented by the formula:

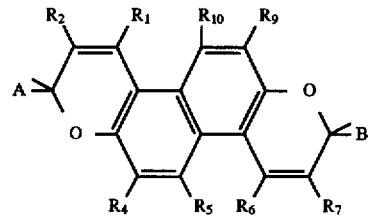

wherein A and B are each selected from the following group: a substituted divalent cyclic radical, a substituted divalent aromatic radical, and a substituted divalent fused heterocyclic radical.

10 Claims, No Drawings

PHOTOCHROMIC SPIRONAPHTHOPYRAN COMPOUNDS

BACKGROUND OF THE INVENTION

The present invention generally relates to naphthopyran compounds. More specifically, the present invention relates to photochromic spironaphthopyran compounds.

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the photochromic compound is isolated from the ultraviolet radiation, such as by placing the compound in a dark room.

Various products, including optical lenses, incorporate the principal of photochromism. For example, photochromic compounds, such as naphthopyrans, are incorporated into plastic ophthalmic lenses to effect color changes in the lenses when the lenses are exposed to particular lighting conditions. Additionally, different photochromic compounds may be blended together to create a color effect that is different from respective color effects of the individual photochromic compounds. As an example, a first photochromic compound that turns orange or red when activated by light and a second photochromic compound that turns blue when activated by light may be blended together to form a photochromic mixture that produces a shade of gray when activated by light.

Several types of photochromic compounds have been reported which exhibit changes in color when exposed to ultraviolet light. One particular class of photochromic compounds includes the 3,3-disubstituted naphthopyrans. One specific group of 3,3-disubstituted naphthopyrans includes the 3H-naphtho [2,1b]pyrans. The color response of the 3H-naphtho[2,1b]pyrans to ultraviolet light extends to purple, red, orange, or yellow, depending upon the composition and structure of the particular 3H-naphtho[2,1b] pyrans. A general expression of the 3H-naphtho[2,1b]pyrans is provided in graphical formula I:

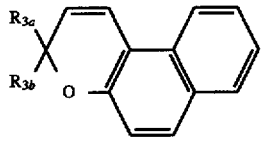

where $R_{3a}$ and $R_{3b}$ are substituents attached to the pyran ring at the position indicated.

U.S. Pat. No. 3,567,605 to Becker describes chromenes and chromene derivatives which are photochromic at relatively low temperature. The Becker patent also describes chromenes and chromene derivatives which are photochromic at room temperature, such as diphenyl-3H-naphtho[2,1b]pyran, where $R_{3a}$ and $R_{3b}$ of formula I are each phenyl groups.

U.S. Pat. No. 4,931,221 to Heller et al. describes additional photochromic compounds, including 3H-naphtho[2,1b] pyrans represented by formula I, where $R_{3a}$ and $R_{3b}$ are cyclopropyl radicals and where any of various substituents are included on the naphtho portion of the naphthopyran rings. Heller reports that the 3H-naphtho[2,1b]pyrans which include cyclopropyl radicals exhibit a larger bathochromic shift in the visible spectrum, as compared to 3H-naphtho[2,1b]pyrans which include alkyl groups or a spirocyclo-alkyl group in place of the cyclopropyl radicals.

U.S. Pat. No. 5,066,818 to Gemert et al. discloses additional photochromic compounds generally meeting graphical formula I. The Gemert patent reports a range of decolorization rates associated with the 3H-naphtho [2,1b]pyrans.

U.S. Pat. No. 5,106,998 to Tanaka et al. describes compounds in which $R_{3a}$ and $R_{3b}$ of graphical formula I are alkyl groups. Tanaka reports several fade times and maximum absorption wavelengths associated with the compounds.

U.S. Pat. No. 5,238,981 to Knowles describes naphthopyran compounds of graphical formula I in which $R_{3a}$ and $R_{3b}$ are each selected from a group of organic radicals that include phenyl and naphthyl. Various potential substitutions on the naphtho portion of the naphthopyrans ring are taught, including an 8-methoxy substitution. Knowles states that number eight carbon atom substitutions, such as the 8-methoxy substitution, cause a bathochromic shift in the visible spectrum associated with activated forms of the 3H-naphtho [2,1b]pyrans and in the ultraviolet spectrum of unactivated forms of the 3H-naphtho[2,1b]pyrans.

U.S. Pat. No. 5,244,602 to Van Gemert and U.S. Pat. No. 5,274,132 to Van Gemert each describe 3H-naphtho[2,1b] pyrans of graphical formula I that include various radical substitutions at the $R_{3a}$ and $R_{3b}$ positions. Each of these Van Gemert patents also claim to achieve bathochromic shifts in the visible spectrum associated with the 3H-naphtho[2,1b] pyrans.

Another class of photochromic compounds include spironaphtho pyrans, as expressed in graphical formula II:

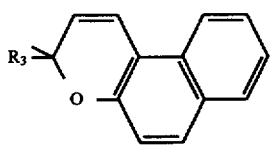

In formula II, $R_3$ is attached to the pyran ring by a spiro carbon, which is a single carbon atom that is shared by two separate rings. Compounds with a single carbon atom that is common to two separate rings are called spiro compounds. Very few naphthopyrans have been disclosed in which the carbon in the number 3 position of the naphthopyran ring is a spiro carbon.

U.S. Pat. No. 4,826,977 to Heller describes a naphthopyran of formula II where $R_3$ is the adamantyl group. Another patent, U.S. Pat. No. 4,980,089 to Heller, teaches a naphthopyran of formula II where $R_3$ may be a bicyclic norcamphane group, a tricyclodecane group, or derivatives of either the norcamphane group or the tricyclodecane group.

Additionally, U.S. Pat. No. 5,106,998 to Tanaka et al. describes pyran compounds, such as that of graphical formula II, in which $R_3$ is either a norbornylidene radical or a bicyclo[3,3,1]9-nonylidene radical. Tanaka reports several fade times and maximum absorption wavelengths associated with various naphthopyrans that include either the norbornylidene or the bicyclo[3,3,1]9-nonylidene radical.

SUMMARY OF THE INVENTION

The present invention includes a naphthopyran compound represented by the formula:

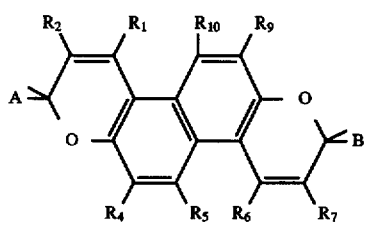

wherein A and B are each selected from the following group: a substituted divalent cyclic radical, a substituted divalent aromatic radical, and a substituted divalent fused heterocyclic radical.

DETAILED DESCRIPTION OF THE PREFERRED EMBODIMENTS

Novel photochromic compounds have been discovered which enable high wavelength activation and deep coloring. On activation, the novel photochromic compounds produce colors that are capable of being blended with blue-producing photochromic compounds to form photochromic blends that produce remarkably pleasing gray colors when the blends are activated by ultraviolet radiation. Furthermore, the novel photochromic compounds have acceptable fade rates and may therefore be desirably incorporated into a variety of photochromic articles.

The novel naphthopyran compounds of the present invention may be generally represented by graphic formula III as follows:

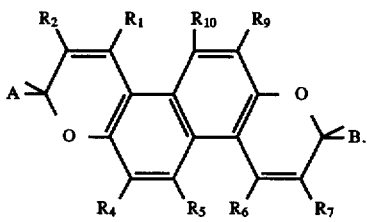

For purposes of the present application, including the description and the claims, it is to be understood that graphical formula III includes all structural isomers of the compounds represented by graphical formula III.

A variety of substituents may be placed on the pyran portion and the naphtho portion of the spiro naphthopyrans of the present invention. For example, any of the positions represented in graphic formula III by $R_1$, $R_2$, $R_4$, $R_5$, $R_6$, $R_7$, $R_9$, and $R_{10}$ may be filled with any of the following: hydrogen; a stable organic radical, such as alkyl, alkoxy, substituted or unsubstituted phenyl, unsubstituted or substituted phenoxy, naphthyl, naphthoxy, cycloalkyl, furyl, alkoyl, alkoyloxy, aroyl, or aroyloxy; a heterocyclic group; a halogen; a nitrogen-substituted group, such as amino, dialkylamino or nitro; or a nitrogen-substituted ring compound, such as morpholino, piperidino, or piperazino.

Also in graphic formula III, the positions represented by A and B may be filled by any substituted divalent cyclic radical, any substituted aromatic radical, or any substituted divalent fused heterocyclic radical. A and B may be filled with the same divalent radical, or A and B may be filled with different divalent radicals. The substituents of the divalent cyclic radical, the divalent aromatic radical and the divalent fused heterocyclic radical may be hydrogen or any stable organic radical, such as alkyl, alkoxy, substituted or unsubstituted phenyl, substituted or unsubstituted phenoxy, naphthyl, naphthoxy, cycloalkyl, furyl, alkoyl, alkoyloxy, aroyl, or aroyloxy. Additionally, the substituents of the divalent cyclic radical, the divalent aromatic radical and the divalent fused heterocyclic radical may also be substituted with alkyl, alkoxy, phenyl, phenoxy, naphthyl, naphthoxy, cyclo alkyl, furyl, alkoyl, alkoyloxy, aroyl, or aroyloxy.

The compounds represented by graphic formula III are derivatives of aryl chromenes known as spironaphthopyrans. These inventive spironaphthopyran compounds exhibit a surprising and highly desirable bathochromic shift of the maximum activated wavelength. The bathochromic shift exhibited by the inventive spironaphthopyran compounds provides photochromic species which turn orange, reddish-orange, or red when activated by an ultraviolet radiation source, such as solar radiation or light radiated from a mercury or xenon lamp.

It has been found desirable to produce photochromic compounds with maximum activated wavelengths approaching and even exceeding 500 nanometers. Photochromic compounds with maximum activated wavelengths near or above 500 nanometers change from original states of color to deep shades of orange, reddish-orange, or red when activated by ultraviolet light. The colored forms of the activated photochromic compounds fade to the original, unactivated color states at ambient temperatures when isolated from the ultraviolet light. As used in this disclosure, "intense photochromes" refers to photochromic compounds that turn deep shades of orange, reddish orange, or red when activated.

The inventive naphthopyrans represented by graphic formula III, especially the intense photochromes, exhibit a deep color and a larger bathochromic shift in the visible spectrum of the activated state as compared to existing naphthopyrans. Indeed, many of the inventive naphthopyrans represented by graphic formula III, especially the intense photochromes, approach a maximum activated wavelength of 500 nanometers and exhibit deep shades of orange, reddish-orange, or red when activated by ultraviolet light. Surprisingly, one preferred naphthopyran of the represented by graphic formula III actually exceeds the 500 nanometer maximum activated wavelength level.

Acceptable spironaphthopyran compounds of the present invention have a maximum activated wavelength of at least about 472 nanometers, when dissolved in chloroform. More preferably, the inventive spironaphthopyrans have a maximum activated wavelength of at least about 490 nanometers, when dissolved in chloroform. Still more preferably, the spironaphthopyrans of the present invention have maximum activated wavelengths of at least about 502 nanometers, when dissolved in chloroform.

The intense spironapthopyrans of the present invention may be blended with one or more other photochromic compounds having maximum activation wavelengths different from that of the inventive intense photochromes to make photochromic mixtures. Preferably, the other photochromic compounds turn colors other than orange, reddish orange and red when activated with ultraviolet light. In one embodiment, one or more of the inventive intense photochromes is preferably blended with another photochromic compound, which has a different maximum activation wavelength and which turns blue when activated with ultraviolet light, to make the photochromic mixture. It has been discovered that photochromic mixtures that include blends of the inventive intense photochromes and blue-turning photochromic compounds change to pleasing, desirable, intense shades of gray when activated by ultraviolet light, such as that present in sunlight. The inventive spironaphthopyrans, or the photochromic mixtures that include the inventive spironaphthopyrans, may be desirably applied as coatings to, or incorporated within, articles, such as conventional synthetic plastic materials often used for optical elements.

One suitable method of preparing photochromic compounds having the structure of graphic formula III involves reacting a suitable ketone precursor with a metal salt of an alkyne to make an intermediate. The intermediate is then reacted with either an unsubstituted naphthol or a substituted naphthol in the presence of a catalyst. The resultant material is then purified by recrystallization, column chromatography, or a combination of recrystallization and column chromatography.

Suitable ketone precursors may be represented by graphic formula IV:

where the position represented by R is filled by the substituted divalent cyclic, the substituted aromatic radical, or the substituted divalent fused heterocyclic radical described with reference to graphic formula III. As already indicated, the substituents of the substituted divalent cyclic, the substituted aromatic radical, or the substituted divalent fused heterocyclic radical may be hydrogen or a stable organic radical such as alkyl, alkoxy, substituted or unsubstituted phenyl, substituted or unsubstituted phenoxy, naphthyl, naphthoxy, cycloalkyl, furyl, alkoyl, alkoyloxy, aroyl, or aroyloxy. Some examples of suitable ketone precursors consistent with graphical formula IV are shown below:

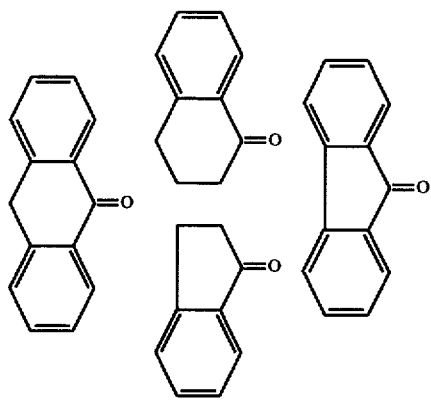

The metal salt of the alkyne is preferably lithium acetylide and the organic solvent is preferably tetrahydrofuran. The naphthol is preferably 2,6-dihydroxynaphthalene. The catalyst is preferably a catalytic amount of p-toluene sulfonic acid.

One particularly effective naphthopyran compound, consistent with graphic formula III, has the structure of graphic formula V:

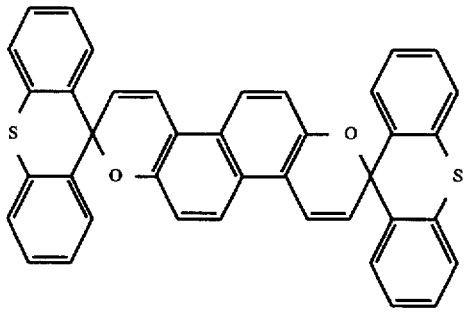

This compound has an activated maximum wavelength of absorption, when dissolved in chloroform, of about 502 nanometers when irradiated with ultraviolet light. Additionally, when activated by ultraviolet light, the naphthopyran of formula V turns a deep shade of red. Furthermore, the naphthopyran of formula V blends with blue-turning photochromic compounds, such as substituted spiroindolino naphthoxazine, to advantageously make one of the photochromic compound blends that changes to a desirable, intense shade of gray when activated by ultraviolet radiation.

The naphthopyran compound represented by graphic formula III may be used in many applications of plastic substrates. For example, compounds represented by graphic formula III may be incorporated into a host material that is applied to an article. Also, compounds represented by graphic formula III may be combined with the host material to make the article. Additionally, compositions that contain one or more of the photochromic compounds represented by graphic formula III, such as the previously mentioned photochromic mixtures, may be incorporated into the host material. The combination of the composition and host material, as already noted, may be applied to the article or may be used to make the article. Also, compounds represented by graphic formula III and compositions containing one or more compounds represented bit graphic formula III may be applied to or coated onto the host material, the article, or other suitable substrate.

Polymerized organic materials, such as synthetic polymerized plastics often used to make optical elements, are examples of the host material. Examples of the article include optical elements, such as plano and ophthalmic lenses. Non-exhaustive illustrations of suitable synthetic polymerized plastics for use as the host material include polyacrylate, polycarbonate, polyvinyl alcohol, polyvinyl acetate, polyvinyl chloride, polyurethane, cellulose ester and bis-polyol (allyl carbonate) monomer-based polymer.

As used in this disclosure, the term bis-polyol (allyl carbonate) monomer and similar phrases are intended to mean and include the named monomer or prepolymer and any related monomer series contained therein. Some non-limiting examples of bis-polyol (allyl carbonate) monomers include ethylene glycol bis(allyl carbonate), diethylene glycol bis(2-methylallyl carbonate), diethylene glycol bis(allyl carbonate), propylene glycol bis(2-ethylallyl carbonate), 1-3-propanediol bis(allyl carbonate), 1,3-butanediol bis (allyl carbonate), 1,4-butanediol bis(2,bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

The mount of a particular one of the compounds represented by graphic formula III, or a particular composition containing one of the compounds represented by graphic formula III, that is incorporated into the host material or the coating material is defined, for purposes of this disclosure, as the photochromic mount. The photochromic amount is not critical, provided that a sufficient mount to produce a photochromic effect perceptible to the human eye is used. The photochromic amount often depends on the desired intensity of the color on activation of the particular inventive naphthopyran and on the method of incorporation or application of the particular inventive naphthopyran. Typically, the photochromic mount incorporated into or applied to the host material or incorporated into the coating material ranges from about 0.01 to about 20 percent by weight, based on the weight of the host material or the weight of the coating material, as applicable.

The present invention is more particularly described in the following examples which are intended as illustrations only since numerous modifications and variations within the scope of the general formulation will be apparent to those skilled in the art.

EXAMPLE 1

Step 1

In this example, the ketone precursor was 9-fluorenone. In subsequent examples, the ketone precursor is referred to as compound K. In this example, five grams of the ketone precursor, 9-fluorenone, were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in solvent and the solvent solution was cooled to yield a recrystallized compound. Nuclear magnetic resonance (NMR) spectroscopy showed the recrystallized compound to be 9,9 fluorenediyl propargyl alcohol, a relatively pure propargyl alcohol.

Step 2

Three grams of the 9,9 fluorenediyl propargyl alcohol prepared in Step 1 were mixed with 1.25 grams of 2,6-dihydroxy naphthalene in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the hexane solution was cooled to yield a recrystallized product. The recrystallized product was shown, by nuclear magnetic resonance (NMR) spectroscopy, to contain the following 3H-naphtho[2,1-b] pyran:

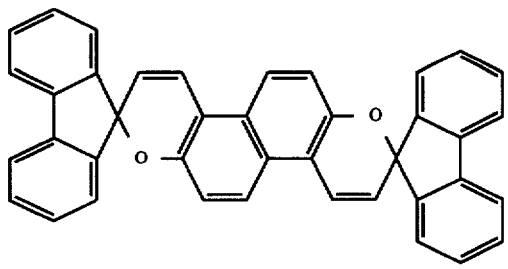

or its structural isomer. In subsequent examples, the 3H-naphtho[2,1-b]pyran product is referred to as product P.

EXAMPLE 2

The procedure of Example 1 was repeated in Example 2 except that the compound K used in Example 2 was thioxanthen-9-one; the propargyl alcohol produced in Step 1 was other than 9,9 fluorenediyl propargyl alcohol; the amount of substituted propargyl alcohol from Step 1 that was used in Step 2 was 3.1 grams; and the product P was shown, by nuclear magnetic resonance (NMR) spectroscopy, to contain the following substituted 3H-naphtho[2,1-b]pyran:

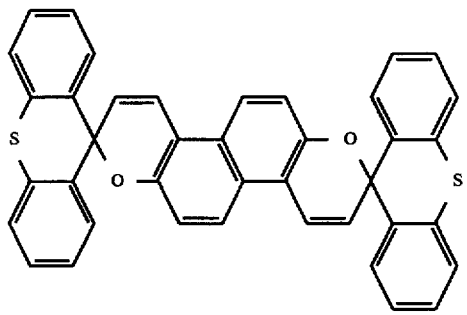

or its structural isomer.

EXAMPLE 3

The procedure of Example 1 was repeated in Example 3 except that the compound K used in Example 3 was 7-methoxy-1-tetralone; the propargyl alcohol produced in Step 1 was other than 9,9 fluorenediyl propargyl alcohol; the amount of propargyl alcohol from Step 1 that was used in Step 2 was 2.4 grams; the amount of 2,6-dihydroxynaphthalene that was used in Step 2 was 1.25 grams; and the product P was shown, by nuclear magnetic resonance (NMR) spectroscopy, to contain the following substituted 3H-naphtho[2,1-b]pyran:

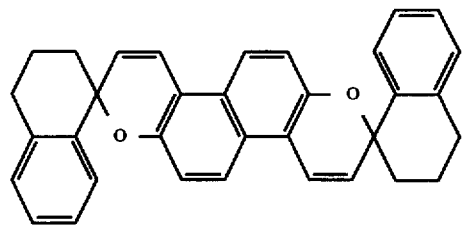

or its structural isomer.

COMPARATIVE EXAMPLE 1

Step 1

Five grams of benzophenone were placed together with five grams of lithium acetylide in 250 milliliters of tetrahydrofuran and stirred for 72 hours. The resultant mixture was poured over ice and diluted with water to form an organic layer and an aqueous layer. The organic layer was separated from the aqueous layer and dried with anhydrous sodium sulfate. The dried organic layer was evaporated to obtain a solid material. The solid material was then triturated with acetone. The triturated material was dissolved in a solvent and the solvent solution was cooled to yield a recrystallized compound. Nuclear magnetic resonance (NMR) spectroscopy showed the resultant material to be a relatively pure substituted propargyl alcohol, diphenyl propargyl alcohol.

Step 2

Two grams of the substituted propargyl alcohol formed in step 1, diphenyl propargyl alcohol, were mixed with a stoichiometric amount, 1.71 grams, of 6-methoxy-2-naphthol in 200 milliliters of benzene. Twenty milligrams of p-toluenesulfonic acid were then added and the mixture was stirred under reflux for 8 hours. The resultant mixture was cooled and washed with 10% aqueous sodium hydroxide. The organic solvent (benzene) was removed using a rotary evaporator. The resulting material was dissolved in hexane and the hexane solution was cooled to yield a recrystallized product. The recrystallized product was shown, by nuclear magnetic resonance (NMR) spectroscopy, to be 3,3-diphenyl-8-methoxy-3H-naphtho[2,1-b]pyran, a substituted 3H-naphtho[2,1-b]pyran.

DETERMINATION OF MAXIMUM ABSORPTION WAVELENGTH AND FADE TIME

Each of the photochromic compounds (compound P) formed in step 2 of Examples 1–3 and in Comparative Example 1 were independently dissolved in separate containers of chloroform. Additionally, a purchased sample of 3,3-diphenyl-naphtho-3H[2,1-b]pyran, identified as Comparative Example 2, was dissolved in a separate container of chloroform.

Each of the chloroform-dissolved photochromic compounds of Examples 1–3 and Comparative Examples 1–2 were then irradiated with ultraviolet light with a maximum wavelength of 350 nanometers, and the maximum absorption wavelength $\lambda_{max}$ was determined for each of the chloroform-dissolved photochromic compound. The fade time, $T_{1/2}$ was then determined for each of the irradiated compounds. The fade time for a particular chloroform dissolved photochromic compound is defined as the time interval, at room temperature (72° F.), for the absorbance of the activated form of the chloroform-dissolved photochromic compound to decrease to one half of the maximum absorbance, after the photochromic compound is isolated from the activating source of ultraviolet light. The maximum absorption wavelength and fade time determined for each of the irradiated photochromic compounds of Examples 1–3 and Comparative Examples 1–2 are presented in Table 1:

TABLE 1

| | Chloroform | $T_{1/2}$ (Seconds) Chloroform |
|---|---|---|
| COMPOUND EXAMPLE | | |
| 1 | 490 | * |
| 2 | 502 | 1.9 |
| 3 | 472 | >180 |
| COMPARATIVE EXAMPLE | | |
| 1 | 472 | 10 |
| 2 | 435 | 13 |

Comparative Example 2: Purchased 3,3-diphenyl-naphtho-3H[2,1-b]pyran
* Fades too fast to obtain readings The values presented in Table 1 illustrate that the photochromic compounds of Examples 1 and 2 each have a longer maximum wavelength of activation than does the photochromic compound of Comparative Example 1, 3,3-diphenyl-8-methoxy-3H-naphtho[2,1-b]pyran. The Table 1 values also illustrate that the photochromic compounds of Examples 1–3 exhibit longer maximum wavelengths of activation than does the photochromic compound of Comparative Example 2, 3,3-diphenyl-naphtho-3H[2,1-b]pyran. The longer maximum wavelengths of activation exhibited by the inventive photochromic compounds of Examples 1–3 are desirable characteristics for substituted naphthopyran photochromic compounds.

Although the present invention has been described with reference to preferred embodiments, workers skilled in the art will recognize that changes may be made in form and detail without departing from the spirit and scope of the invention.

What is claimed is:

1. A naphthopyran compound represented by the formula:

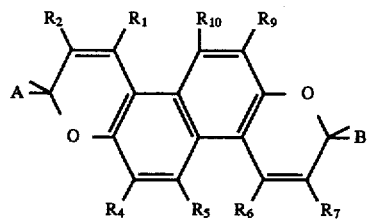

wherein $R_1$, $R_2$, $R_6$, and $R_7$ are each hydrogen;

wherein $R_4$, $R_5$, $R_9$, and $R_{10}$ are each selected from the group consisting of hydrogen, alkyl, alkoxy, phenyl, phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino;

wherein A and B are

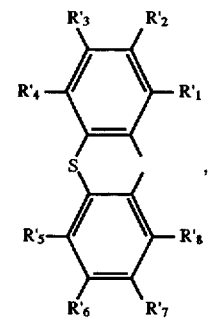

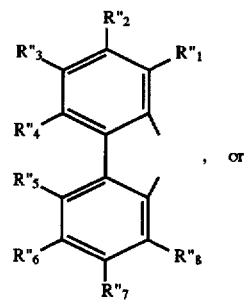, or

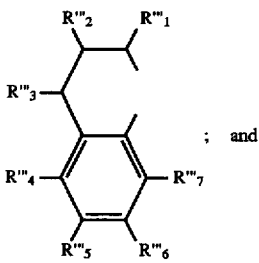; and wherein $R'_1$, $R'_2$, $R'_3$, $R'_4$, $R'_5$, $R'_6$, $R'_7$, $R''_1$, $R''_2$, $R''_3$, $R''_4$, $R''_5$, $R''_6$, $R''_7$, $R''_8$, $R'''_1$, $R'''_2$, $R'''_3$, $R'''_4$, $R'''_5$, $R'''_6$, and $R'''_7$ are selected from the group consisting of hydrogen, alkyl, alkoxy, phenyl, phenoxy, naphthyl, naphthoxy, cycloalkyl, furyl, alkoyl, alkoyloxy, aroyl, and aroyloxy.

2. The naphthopyran compound of claim 1 wherein $R_4$, $R_5$, $R_9$, and $R_{10}$ are each selected from the group consisting of $C_1$–$C_2$ alkyl, methoxy and ethoxy.

3. A naphthopyran compound represented by the formula:

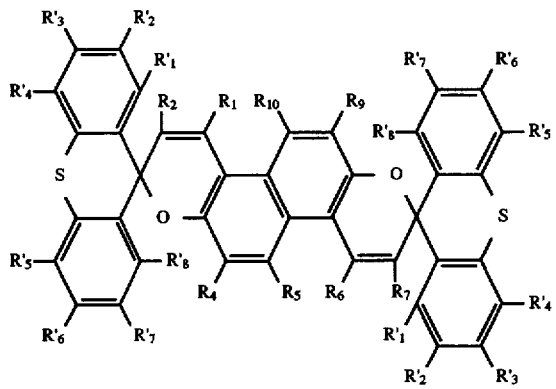

wherein $R_1$, $R_2$, $R_6$, and $R_7$ are each hydrogen;

wherein $R_4$, $R_5$, $R_9$, and $R_{10}$ are each selected from the group consisting of hydrogen, alkyl, alkoxy, phenyl, naphthyl, cycloalkyl, furyl, alkoyl, alkoyloxy, aroyl, aroyloxy, halogen, amino, dialkylamino, nitro, morpholino, piperidino, and piperazino; and wherein $R'_1$, $R'_2$, $R'_3$, $R'_4$, $R'_5$, $R'_6$, $R'_7$, $R'_8$ are selected from the group consisting of hydrogen, alkyl, alkoxy, phenyl, phenoxy, naphthyl, naphthoxy, cycloalkyl, furyl, alkoyl, alkoyloxy, aroyl, and aroyloxy.

4. The naphthopyran compound of claim 3 wherein $R_4$, $R_5$, $R_9$, and $R_{10}$ are each selected from the group consisting of $C_1$–$C_2$ alkyl, methoxy and ethoxy.

5. The naphthopyran compound of claim 3 wherein $R_4$, $R_5$, $R_9$, and $R_{10}$ are each selected from the group consisting of $C_1$–$C_2$ alkyl, methoxy and ethoxy.

6. The naphthopyran compound of claim 3 wherein $R_4$, $R_5$, $R_9$, and $R_{10}$ are each selected from the group consisting of $C_1$–$C_2$ alkyl, methoxy and ethoxy.

7. A naphthopyran compound represented by the formula:

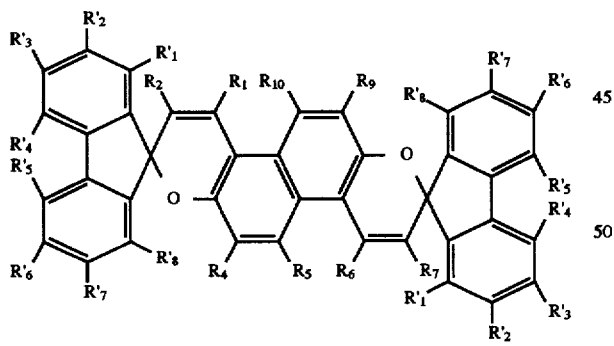

wherein $R_1$, $R_2$, $R_6$, and $R_7$ are each hydrogen;

wherein $R_4$, $R_5$, $R_9$, and $R_{10}$ are each selected from the group consisting of hydrogen, alkyl, alkoxy, phenyl, naphthyl, cycloalkyl, furyl, alkoyl, alkoyloxy, aroyl, aroyloxy, halogen, amino, dialkylamino, nitro, morpholino, piperidino, and piperazino; and wherein $R'_1$, $R'_2$, $R'_3$, $R'_4$, $R'_5$, $R'_6$, $R'_7$, $R'_8$ are selected from the group consisting of hydrogen, alkyl, alkoxy, phenyl, phenoxy, naphthyl, naphthoxy, cycloalkyl, furyl, alkoyl, alkoyloxy, aroyl, and aroyloxy.

8. A naphthopyran compound represented by the formula:

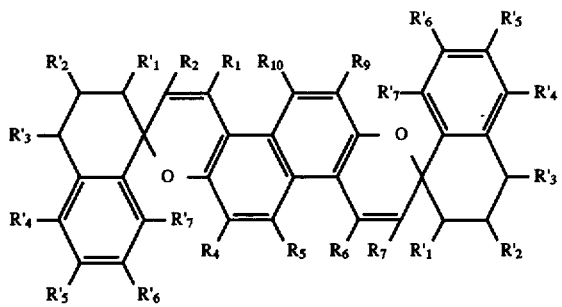

wherein $R_1$, $R_2$, $R_6$, and $R_7$ are each hydrogen;

wherein $R_4$, $R_5$, $R_9$, and $R_{10}$ are each selected from the group consisting of hydrogen, alkyl, alkoxy, phenyl, naphthyl, cycloalkyl, furyl, alkoyl, alkoyloxy, aroyl, aroyloxy, halogen, amino, dialkylamino, nitro, morpholino, piperidino, and piperazino; and wherein $R'_1$, $R'_2$, $R'_3$, $R'_4$, $R'_5$, and $R'_7$ are selected from the group consisting of hydrogen, alkyl, alkoxy, phenyl, phenoxy, naphthyl, naphthoxy, cycloalkyl, furyl, alkoyl, alkoyloxy, aroyl, and aroyloxy.

9. A naphthopyran compound represented by the formula:

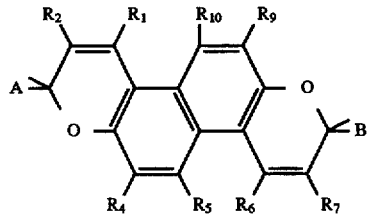

wherein $R_1$, $R_2$, $R_6$, and $R_7$ are each hydrogen;

wherein $R_4$, $R_5$, $R_9$, and $R_{10}$ are each selected from the group consisting of hydrogen, alkyl, alkoxy, phenyl, phenoxy, naphthyl, naphthoxy, cycloalkyl, furyl, alkoyl, alkoyloxy, aroyl, aroyloxy, halogen, amino, dialkylamino, nitro, morpholino, piperidino, and piperazino;

wherein A and B are

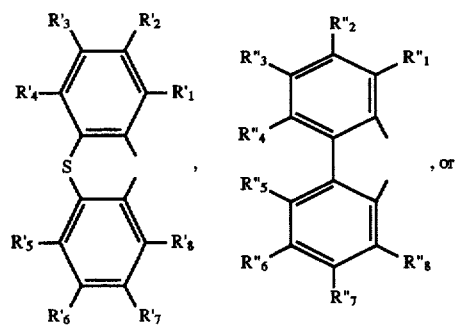

-continued

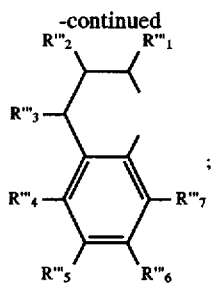

;

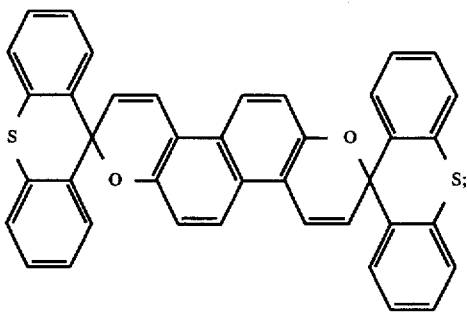

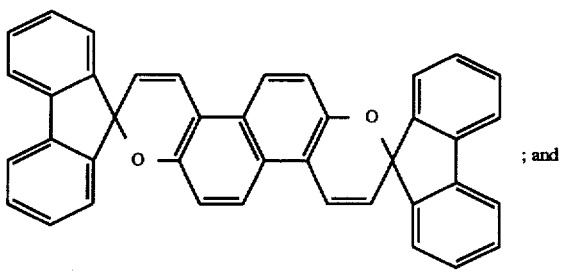
; and

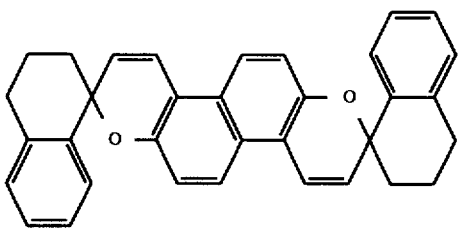
.

wherein $R'_1$, $R'_2$, $R'_3$, $R'_4$, $R'_5$, $R'_6$, $R'_7$, $R'_8$, $R''_1$, $R''_2$, $R''_3$, $R''_4$, $R''_5$, $R''_6$, $R''_7$, $R''_8$, $R'''_1$, $R'''_2$, $R'''_3$, $R'''_4$, $R'''_5$, $R'''_6$, and $R'''_7$ are selected from the group consisting of hydrogen, unsubstituted alkyl, substituted alkyl, unsubstituted alkoxy, substituted alkoxy, unsubstituted phenyl, substituted phenyl, unsubstituted phenoxy, substituted phenoxy, unsubstituted naphthyl, substituted naphthyl, unsubstituted naphthoxy, substituted naphthoxy, unsubstituted cycloalkyl, unsubstituted furyl, substituted furyl, unsubstituted alkoyl, substituted alkoyl, unsubstituted alkoyloxy, substituted alkoyloxy, unsubstituted aroyl, substituted aroyl, unsubstituted aroyloxy, and substituted aroyloxy; and wherein the substituents of the substituted alkyl, substituted alkoxy, substituted phenyl, substituted phenoxy, substituted naphthyl, substituted naphthoxy, substituted cycloalkyl, substituted furyl, substituted alkoyl, substituted alkoyloxy, substituted aroyl, and substituted aroyloxy radicals that can fill any of $R'_1$, $R'_2$, $R'_3$, $R'_4$, $R'_5$, $R'_6$, $R'_7$, $R'_8$, $R''_1$, $R''_2$, $R''_3$, $R''_4$, $R''_5$, $R''_6$, $R''_7$, $R''_8$, $R'''_1$, $R'''_2$, $R'''_4$, $R'''_5$, $R'''_6$, and $R'''_7$ are selected from the group consisting of alkyl, phenyl, phenoxy, naphthyl, naphthoxy, cycloalkyl, furyl, alkoyl, alkoyloxy, aroyl, and aroyloxy.

10. A naphthopyran compound selected from the group consisting of

* * * * *

UNITED STATES PATENT AND TRADEMARK OFFICE
CERTIFICATE OF CORRECTION

PATENT NO. : 5,679,805
DATED : OCTOBER 21, 1997
INVENTOR(S) : FRANK J. HUGHES

It is certified that error appears in the above-indentified patent and that said Letters Patent is hereby corrected as shown below:

In col. 6, at line 25, delete "bit", and insert --by--.

In col. 6, at line 51, delete "mount", and insert --amount--.

In col. 6, at line 56, delete "mount", and insert --amount--.

In col. 6, at line 57, delete "mount", and insert --amount--.

In col. 6, at line 63, delete "mount", and insert --amount--.

In col. 3, at line 57, delete "HI", and insert --III--.

In col. 10, at line 62, delete " $R'_7, R''_1$ ", and insert -- $R'_7, R'_8, R''_1$ --.

In col. 12, at line 25, delete " $R'_5$ and $R'_7$ ", and insert -- $R'_5, R'_6,$ and $R'_7$ In col. 13, at line 32, insert -- $R'''_3$ --, between " $R'''_2$ " and " $R'''_4$ ".

UNITED STATES PATENT AND TRADEMARK OFFICE
CERTIFICATE OF CORRECTION

Page 2 of 2

PATENT NO. : 5,679,805
DATED : OCTOBER 21, 1997
INVENTOR(S) : FRANK J. HUGHES

It is certified that error appears in the above-indentified patent and that said Letters Patent is hereby corrected as shown below:

At col. 5, lines 12-15, please delete the following formula:

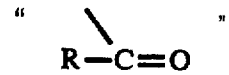

and insert the following formula:

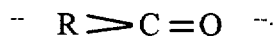

Signed and Sealed this

Fourteenth Day of July, 1998

Attest:

BRUCE LEHMAN

*Attesting Officer*  *Commissioner of Patents and Trademarks*